United States Patent
Yang

(10) Patent No.: US 10,265,032 B2
(45) Date of Patent: Apr. 23, 2019

(54) SYSTEMS AND METHODS FOR DATA COLLECTION IN A MEDICAL DEVICE

(71) Applicant: SHANGHAI UNITED IMAGING HEALTHCARE CO., LTD., Shanghai (CN)

(72) Inventor: Longzi Yang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 15/942,704

(22) Filed: Apr. 2, 2018

(65) Prior Publication Data

US 2018/0256119 A1    Sep. 13, 2018

Related U.S. Application Data

(63) Continuation of application No. PCT/CN2016/111353, filed on Dec. 21, 2016.

(30) Foreign Application Priority Data

Dec. 29, 2015  (CN) .......................... 2015 1 1015708
Apr. 28, 2016  (CN) .......................... 2016 1 0278818

(51) Int. Cl.
*G06K 9/00*    (2006.01)
*A61B 6/03*    (2006.01)
(Continued)

(52) U.S. Cl.
CPC .............. *A61B 6/032* (2013.01); *A61B 5/055* (2013.01); *A61B 6/4233* (2013.01); *G16H 30/00* (2018.01); *A61B 6/548* (2013.01); *A61B 6/563* (2013.01)

(58) Field of Classification Search
CPC ....... A61B 6/037; A61B 6/032; A61B 6/4266; A61B 6/4494; A61B 6/485; A61B 6/548;
(Continued)

(56) References Cited

U.S. PATENT DOCUMENTS 4,491,734 A      1/1985  Yamaguchi et al.
4,969,166 A *  11/1990  Hahn ..................... A61B 6/032
                                                                      378/19
(Continued)

FOREIGN PATENT DOCUMENTS

CN         101004764 A      7/2007
CN         203314980 U      12/2013
(Continued)

OTHER PUBLICATIONS

International Search Report in PCT/CN2016/111353 dated Mar. 22, 2017, 6 pages.
(Continued)

*Primary Examiner* — Avinash Yentrapati
(74) *Attorney, Agent, or Firm* — Metis IP LLC

(57) ABSTRACT

The present disclosure relates to a data acquisition device and a configuration method. The device includes a channel, wherein the channel includes a data control panel and a plurality of detection components. At least one of the plurality of detection components is directly connected to the data control panel. The data control panel may be configured to identify the channel and send a configuration command to the plurality of detection components. The plurality of detection components may determine channel location numbers of the plurality of detection components based on the configuration command and send the channel location numbers to the data control panel. The data control panel may determine identification numbers for the plurality of detection components based on the channel location
(Continued)

numbers and allocate the identification numbers to the plurality of detection components.

20 Claims, 12 Drawing Sheets

(51) Int. Cl.
*A61B 5/055* (2006.01)
*G16H 30/00* (2018.01)
*A61B 6/00* (2006.01)

(58) Field of Classification Search
CPC ..... A61B 6/563; G01T 1/2985; G01T 1/1647; G01T 1/161; G01T 1/1642; G01T 1/1648; G01T 1/172; G01T 1/2018; G01T 1/208
See application file for complete search history.

(56) References Cited

U.S. PATENT DOCUMENTS

| | | | | |
|---|---|---|---|---|
| 8,921,796 | B1* | 12/2014 | Arseneau | G01T 1/171 |
| | | | | 250/362 |
| 2003/0021455 | A1* | 1/2003 | Dixon | A61B 6/4233 |
| | | | | 382/132 |
| 2003/0031353 | A1* | 2/2003 | Baertsch | A61B 6/00 |
| | | | | 382/132 |
| 2006/0065825 | A1* | 3/2006 | Ishitsu | G01T 1/2985 |
| | | | | 250/252.1 |
| 2007/0152162 | A1* | 7/2007 | Griesmer | G01T 1/2985 |
| | | | | 250/363.09 |
| 2009/0022276 | A1* | 1/2009 | Ohara | A61B 6/00 |
| | | | | 378/101 |
| 2009/0108208 | A1* | 4/2009 | Yanagita | G01T 1/2985 |
| | | | | 250/370.01 |
| 2009/0128713 | A1* | 5/2009 | Kwon | H04N 5/50 |
| | | | | 348/731 |
| 2011/0080993 | A1* | 4/2011 | Hoffman | A61B 6/032 |
| | | | | 378/19 |
| 2011/0173347 | A1 | 7/2011 | Steiner et al. | |
| 2011/0210255 | A1* | 9/2011 | Kim | G01T 1/2985 |
| | | | | 250/362 |
| 2012/0230463 | A1* | 9/2012 | Morton | G01T 1/2985 |
| | | | | 378/6 |
| 2013/0062526 | A1* | 3/2013 | Tsuda | G01T 1/172 |
| | | | | 250/362 |
| 2013/0148873 | A1* | 6/2013 | Arenson | G06T 11/005 |
| | | | | 382/132 |
| 2014/0177806 | A1* | 6/2014 | Tachikawa | A61B 6/4494 |
| | | | | 378/114 |
| 2018/0175956 | A1* | 6/2018 | Xie | G01T 1/161 |

FOREIGN PATENT DOCUMENTS

| | | |
|---|---|---|
| CN | 104184473 A | 12/2014 |
| CN | 104622457 A | 5/2015 |
| CN | 105686830 A | 6/2016 |

OTHER PUBLICATIONS

First Office Action in Chinese Application No. 201511015708.5 dated Feb. 23, 2018, 15 pages.
First office Action in Chinese Application No. 201610278818.9 dated Jul. 10, 2018, 10 pages.

* cited by examiner

SYSTEMS AND METHODS FOR DATA COLLECTION IN A MEDICAL DEVICE

CROSS-REFERENCE TO RELATED APPLICATIONS

This application is a continuation of International Application No. PCT/CN2016/111353, filed on Dec. 21, 2016, which designates the United States of America and claims priority to Chinese Application No. 201511015708.5, filed on Dec. 29, 2015 and Chinese Application No. 201610278818.9, filed on Apr. 28, 2016, contents of which are hereby incorporated by reference in their entireties.

TECHNICAL FIELD

The present disclosure generally relates to medical devices, and in particular, to systems and configuration methods for data acquisition of medical devices.

BACKGROUND

Medical devices, particularly large medical devices, for example, computed tomography (CT) devices, magnetic resonance imaging (MRI) devices, X-ray devices, generally use a data acquisition system to acquire imaging signals. Tens of thousands to hundreds of thousands of sensing units may be used in the data acquisition system, which constitute a plurality of detection components. Recently, how to dynamically configure the data acquisition system and effectively control time management of the detection components during the data acquisition process has become a research focus in the field of medical devices.

SUMMARY

Some embodiments of the present disclosure provide a method for allocating identification number(s) to detection component(s). The method may include the following operations: identifying a channel, wherein the channel may include a data control panel and one or more detection components, and wherein at least one of the one or more detection components may be directly connected to the data control panel; sending, by the data control panel, a configuration command to the one or more detection components; sending, by the one or more detection components, one or more channel location numbers of the one or more detection components to the data control panel based on the configuration command; determining, by the data control panel, one or more identification numbers for the one or more detection components based on the one or more channel location numbers; allocating, by the data control panel the one or more identification numbers to the one or more detection components.

In some embodiments, the identifying the channel may include identifying the channel based on a pin of a detection component that is directly connected to the data control panel.

In some embodiments, the channel may include a plurality of detection components, wherein the plurality of detection components may be connected to the data control panel in parallel, in series, or in a combination thereof.

In some embodiments, the sending, by the data control panel, the configuration command to the one or more detection components may include sending the configuration command by broadcast.

In some embodiments, the method may further include sending the one or more identification numbers to an upper layer software by the data control panel.

In some embodiments, the channel may include a plurality of detection components, wherein the channel location numbers of the plurality of detection components may be different.

In some embodiments, the channel may include a plurality of detection components, wherein the channel location numbers of the plurality of detection components may be continuous.

In some embodiments, the method may further include receiving, by the one or more detection components, a data packet including a clock signal and a sampling triggering command; identifying, by a determination module, a type of a connection between the data control panel and the one or more detection components; determining, by a compensation module, one or more time compensation signals for the one or more detection components based on the type of the connection; performing, by the one or more detection components, sampling based on the time compensation signals, the clock signal, and the sampling triggering command; and sending, by the one or more detection components, a sampling result to the data control panel.

According to some embodiments of the present disclosure, a method is provided. The method may include the following operations: receiving, by one or more detection components, a data packet including a clock signal and a sampling triggering command; identifying, by a determination module, a type of a connection between the data control panel and the one or more detection components; determining, by a compensation module, a time compensation signal for the one or more detection components based on the type of the connection; performing, by the one or more detection components, sampling based on the time compensation signal, the clock signal, and the sampling triggering command; and sending, by the one or more detection components, a sampling result to the data control panel.

In some embodiments, the method may further include identifying, by a clock recovery module, the clock signal based on the Clock and Data Recovery (CDR) technology.

In some embodiments, a frequency of the clock signal may be an integer multiple of a frequency that is used by the one or more detection components for performing simulation integration.

In some embodiments, the identifying the type of the connection between the data control panel and the one or more detection components may include receiving, by the one or more detection components, a configuration command; allocating, by the data control panel, one or more identification numbers to the one or more detection components based on the configuration command; and identifying, by the determination module, the type of the connection between the data control panel and the one or more detection components based on the one or more identification numbers.

In some embodiments, the one or more detection components may include a plurality of detection components, wherein the plurality of detection components are connected to the data control panel in parallel, in series, or in a combination thereof.

In some embodiments, the determining the time compensation signal may include compensating a plurality of detection components with a same time delay when the plurality of detection components are connected to the data control panel in parallel; and compensating the plurality of detection components with different time delays when the plurality of detection components are connected to the data control panel in series.

In some embodiments, the method may further include identifying a channel, wherein the channel may include the data control panel and the one or more detection components, and wherein at least one of the one or more detection components may be directly connected to the data control panel.

According to some embodiments of the present disclosure, a device is provided. The device may include a channel, wherein the channel may include a data control panel and one or more detection components. At least one of the one or more detection components may be directly connected to the data control panel. The data control panel may be configured to identify the channel and send a configuration command to the one or more detection components. The one or more detection components may determine one or more channel location numbers of the one or more detection components based on the configuration command and send the one or more channel location numbers to the data control panel. The data control panel may determine one or more identification numbers for the one or more detection components based on the one or more channel location numbers of the one or more detection components, and allocate the one or more identification numbers to the one or more detection components.

In some embodiments, the data control panel may identify the channel based on a pin of a detection component that is directly connected to the data control panel.

In some embodiments, the channel may include a plurality of detection components, wherein the plurality of detection components may be connected to the data control panel in parallel, in series, or in a combination thereof.

In some embodiments, the sending, by the data control panel, the configuration command to the one or more detection components may include sending the configuration command by broadcast.

In some embodiments, the channel may include a plurality of detection components, and wherein the channel location numbers of the plurality of detection components may be different.

In some embodiments, the channel may include a plurality of detection components, and wherein the channel location numbers of the plurality of detection components may be continuous.

In some embodiments, the device may be a part of a CT system, an MRI system, or an X-ray system.

In some embodiments, the data control panel may send the one or more identification numbers to an upper layer software.

In some embodiments, the one or more detection components may be configured to receive a data packet from the data control panel. The data packet may include a clock signal and a sampling triggering command. At least one of the one or more detection components may include a clock recovery module, a determination module, a compensation module, and an analysis module. The clock recovery module may be configured to identify the clock signal. The determination module may be configured to identify a type of a connection between the data control panel and at least one of the one or more detection components. The compensation module may be configured to determine a time compensation signal for the at least one of the one or more detection components based on the type of the connection between the data control panel and the at least one of the one or more detection components, and compensate the at least one of the one or more detection components with a time delay based on the time compensation signal and the clock signal. The analysis module may be configured to identify the sampling triggering command. At least one of the one or more detection components may be configured to perform sampling based on a compensation result and the sampling triggering command and send a sampling result to the data control panel.

According to some embodiments of the present disclosure, a device is provided. The device may include a data control panel and one or more detection components that are connected to the data control panel. The one or more detection components may receive a data packet from the data control panel. The data packet may include a clock signal and a sampling triggering command. At least one of the one or more detection components may include a clock recovery module, a determination module, a compensation module, and an analysis module. The clock recovery module may be configured to identify the clock signal. The determination module may be configured to identify a type of connection between the data control panel and at least one of the one or more detection components. The compensation module may be configured to determine a time compensation signal for the at least one of the one or more detection components based on the type of connection between the data control panel and the at least one of the one or more detection components and compensate the at least one of the one or more detection components with a time delay based on the time compensation signal and the clock signal. The analysis module may be configured to identify the sampling triggering command. At least one of the one or more detection components may be configured to perform sampling based on a compensation result and the sampling triggering command and send a sampling result to the data control panel.

In some embodiments, the clock recovery module may identify the clock signal based on the Clock and Data Recovery (CDR) technology.

In some embodiments, a frequency of the clock signal may be an integer multiple of a frequency that is used by the one or more detection components for performing simulation integration.

In some embodiments, the identifying, by the determination module, the type of the connection between the data control panel and at least one of the one or more detection components may include receiving, by at least one of the one or more detection components, a configuration command, wherein the data control panel may allocate an identification number to the at least one of the one or more detection components based on the configuration command; and identifying, by the determination module, the type of the connection between the data control panel and the at least one of the one or more detection components based on the identification number.

In some embodiments, the one or more detection components may include a plurality of detection components, wherein the plurality of detection components are connected to the data control panel in parallel, in series, or in a combination thereof.

In some embodiments, the determining, by the compensation module, the time compensation signal may include compensating a plurality of detection components with a same time delay when the plurality of detection components are connected to the data control panel in parallel; and compensating the plurality of detection components with different time delays when the plurality of detection components are connected to the data control panel in series.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

In order to illustrate the technical solutions related to the embodiments of the present disclosure, brief introduction of the drawings referred to the description of the embodiments is provided below. Obviously, drawings described below are only some embodiments of the present disclosure. Those having ordinary skills in the art, without further creative efforts, may apply the present disclosure to other similar scenarios according to these drawings. Unless stated otherwise or obvious from the context, like reference numerals in the drawings refer to like structures or operations.

DETAILED DESCRIPTION

Figure 1:
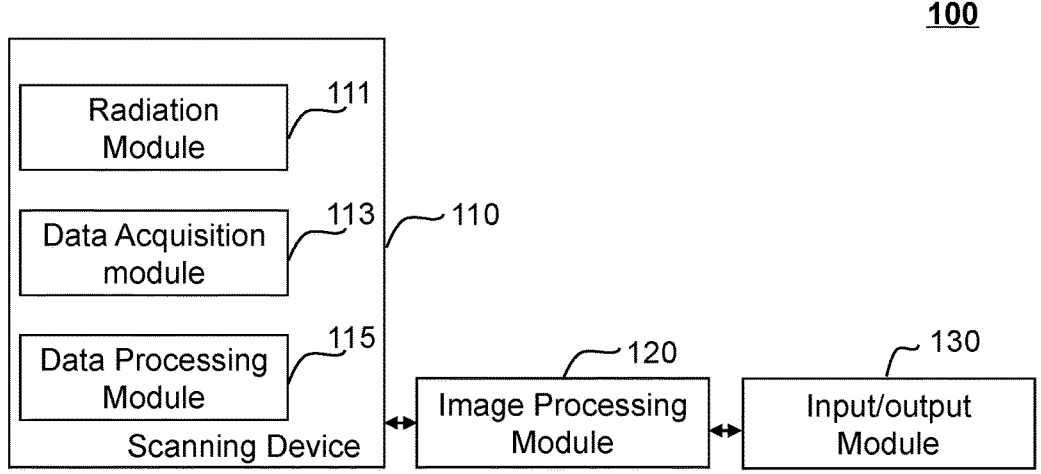
FIG. 1 is a schematic diagram of an exemplary imaging system according to some embodiments of the present disclosure.

In order to illustrate the technical solutions related to the embodiments of the present disclosure, brief introduction of the drawings referred to the description of the embodiments is provided below. Obviously, drawing described below are only some examples or embodiments of the present disclosure. Those having ordinary skills in the art, without further creative efforts, may apply the present disclosure to other similar scenarios according to these drawings. Unless stated otherwise or obvious from the context, like reference numerals in the drawings refer to like structures or operations.

As used in the disclosure and the appended claims, the singular forms "a," "an," and "the" include plural referents unless the content clearly dictates otherwise. It will be further understood that the terms "comprise," "comprising," "include," and/or "including" when used in the disclosure, specify the presence of stated operations and elements, but do not preclude the presence or addition of one or more other operations and elements.

Some modules of the system may be referred to in various ways according to some embodiments of the present disclosure, however, any number of different modules may be used and operated in a client terminal and/or a server. These modules are intended to be illustrative, not intended to limit the scope of the present disclosure. Different modules may be used in different aspects of the system and method.

According to some embodiments of the present disclosure, flow charts are used to illustrate the operations performed by the system. It is to be expressly understood, the operations above or below may or may not be implemented in order. Conversely, the operations may be performed in inverted order, or simultaneously. Besides, one or more other operations may be added to the flowcharts, or one or more operations may be omitted from the flowchart.

Some embodiments of the present disclosure may apply to various imaging systems. Different imaging systems may include a Computed Tomography system, a Magnetic Resonance Imaging system, a Positron Emission Computed Tomography system, etc.

FIG. 1 is a schematic diagram of an exemplary imaging system according to some embodiments of the present disclosure. The imaging system 100 may include a scanning device 110, an image processing module 120, and an input/output module 130. The scanning device 110 may include one or more devices that may be used to scan one or more objects. The device that may be used for scanning may be applied in medical field, for example, medical detection, etc. In some embodiments, the medical detection may include magnetic resonance imaging (MRI), X-ray computed tomography (X-ray CT), positron emission tomography (PET), single-photon emission computed tomography (SPECT), or the like, or any combination thereof. In some embodiments, the object may be an organ, an organism, a substance, a dysfunction, a tumor, or the like, or any combination thereof. In some embodiments, the object may be a head, a chest, an organ, a skeleton, a blood vessel, or the like, or any combination thereof. The scanning device 110 may include a radiation module 111, a data acquisition module 113, and a data processing module 115.

The radiation module 111 may generate a radiation ray for scanning the object. The radiation ray may include a particle ray or a photon ray. The particle ray may include neutrons, protons, electrons, heavy ions, or the like, or any combination thereof. The photon ray may include an X-ray, a γ-ray, an ultraviolet ray, laser, or the like, or any combination thereof. In some embodiments, the radiation module 111 may include a cold cathode ion tube, a high vacuum hot cathode tube, a rotating anode tube, etc. The shape of the radiation ray generated by the radiation module 111 may include a line shape, a narrow pencil shape, a fan shape, a cone shape, a wedge shape, an irregular shape, or the like, or any combination thereof.

The data acquisition module 113 may receive radiation rays from the radiation module 111 or another radiation source. For example, the radiation rays generated by the radiation module 111 may pass through the object and then reach the data acquisition module 113. The data acquisition module 113 may collect data related to the object. Further, the data may be used to construct an image. The data acquisition module 113 may include a detector, and the shape of the detector may be flat, arc-shaped, circular, or the like, or any combination thereof. Merely by way of example, a fan angle of the arc-shaped detector may be any angle between 0° and 360°. The fan angle may be fixed or adjustable according to different situations (e.g., a sensitivity of the detector, a desired resolution of an image, etc.). In some embodiments, the detector may include a plurality of detecting units. The plurality of the detecting units may be arranged in a single row, in two rows, or in other arrangement modes. In some embodiments, the detecting unit may include a scintillation crystal detector, a gas ionization detector, etc.

The data processing module 115 may process the data acquired by the data acquisition module 113. The processing may include pre-processing the received data. Merely by way of example, the pre-processing operation may include amplification, integration, multiplexing, analog-digital conversion, etc. In some embodiments, the data processing module 115 may include a pre-amplifier, an integrator, a multiplexer, an analog-to-digital converter, etc.

The image processing module 120 may acquire information (e.g., scanning data) and process the acquired information. The acquired information may include data generated by the imaging device 110, information stored in another storage module of the imaging system 100, etc. The processing of the information may include reconstructing an image based on the information and performing post-processing on a reconstructed image. The reconstructing an image may include generating an image corresponding to the entire object or one or more parts of the object based on the acquired information. The post-processing may include filtering, noise reduction, a combination operation, or a division operation, etc., on a reconstructed image. The image processing module 120 may include one or more processors (e.g., a central processing unit, an image processing unit, etc.). The one or more processors may be integrated into a physical electronic device, or be part of a server. The electronic device may include a portable computer, a tablet, a mobile phone, a smart terminal device, etc. The server may be a local server or a remote server (e.g., a cloud server). The image processing module 120 may be local or remote.

In some embodiments, the image processing module 120 may include a processor, a microprocessor, a controller, a microcontroller, or the like, or any combination thereof. Specifically, the image processing module 120 may include a central processing unit (CPU), an application specific integrated circuit (ASIC), an application specific instruction set processor (ASIP), a physics processing unit (PPU), a digital processing processor (DSP), a field-programmable gate array (FPGA), a programmable logic device (PLD), or the like, or any combination of thereof.

The input/output module 130 may display an image generated by the image processing module 120 or other data generated by the imaging system 100. In some embodiments, the input/output module 130 may include a display device, for example, a display screen, etc. In some embodiments, the input/output module 130 may perform operations such as rendering, scaling, rotating, maximum intensity projection of an image as needed before displaying a final image. In some embodiments, the input/output module 130 may further include one or more input devices, for example, a keyboard, a touch screen, a touch panel, a mouse, a remote control, or the like, or any combination thereof. A user may input some original parameters and/or set initialization conditions corresponding to image display and/or image processing through the one or more input devices. In some embodiments, the user may perform a setting and/or an operation on the image displayed on the input/output module 130, for example, the setting of displaying a two-dimensional image, displaying a three-dimensional image, displaying an image corresponding to the scanning data, displaying a control interface, displaying an input interface, displaying different areas of an image, displaying a process of image reconstruction, displaying a result of the image construction. In some embodiments, after receiving the user input, the input/output module 130 may perform an operation on the displayed image, such as zooming in, zooming out, displaying a plurality of images simultaneously, or the like, or a combination thereof.

In some embodiments, the scanning device 110, the image processing module 120, and the input/output module 130 may be connected to each other via a wired or wireless connection.

For persons having ordinary skills in the art, after understanding the principle of the system and without deviating the principle, may make various combinations of the modules, constitute a sub-system connected to other modules, or make various variations and modifications on the forms and details of the application filed in which the above method and system may be applied. However, those variations and modifications do not depart from the scope of the disclosure. For example, the above mentioned modules may be different modules embodied in one system, or a single module that can implement functions of two or more modules. For example, in some embodiments of the present disclosure, the scanning device 110 and the image processing module 120 may be integrated into one module. In some embodiments, the image processing module 120 may also process information stored therein.

Figure 2:
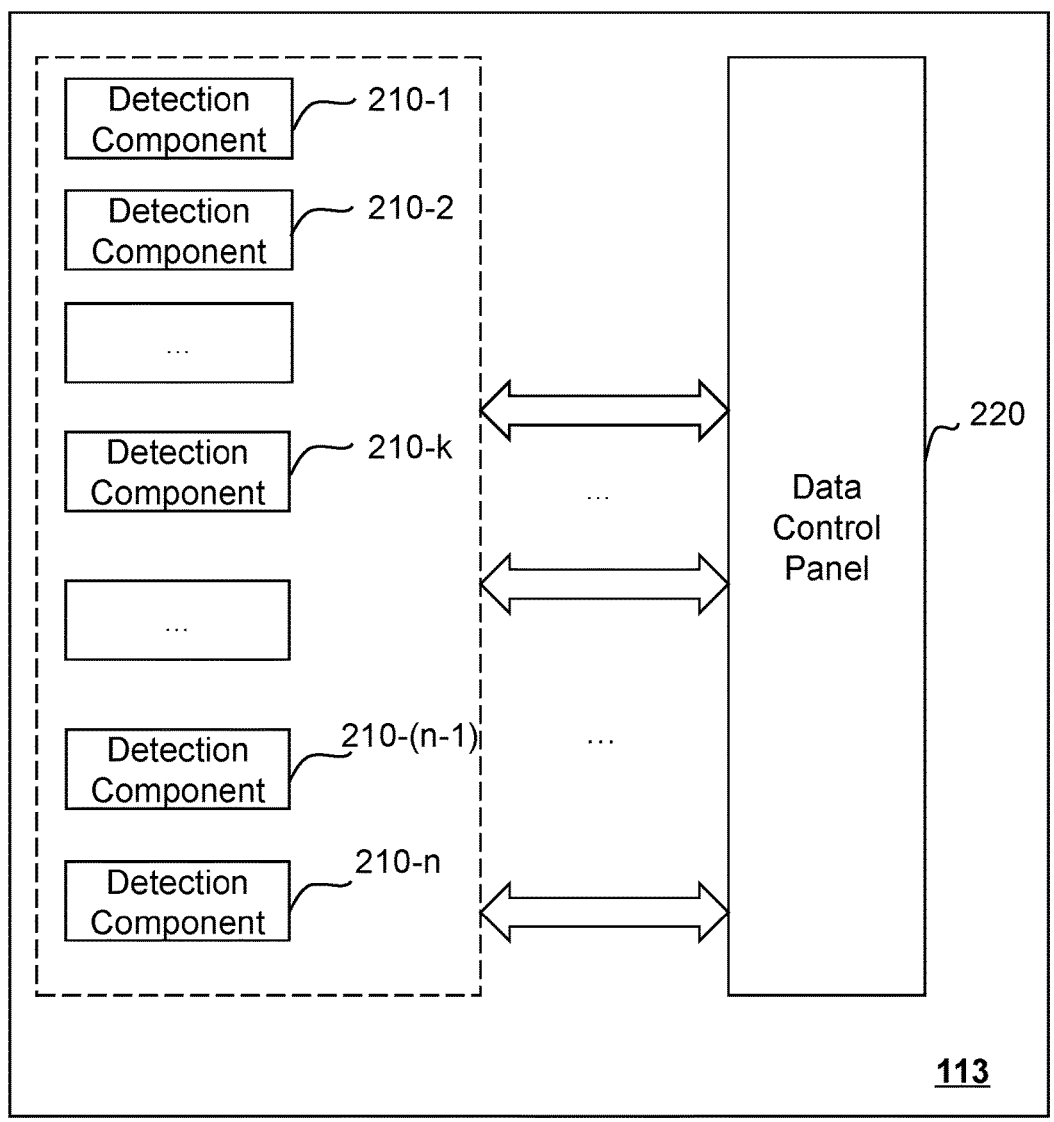
FIG. 2 is a schematic diagram of an exemplary data acquisition module according to some embodiments of the present disclosure.

FIG. 2 is a schematic diagram of an exemplary data acquisition module according to some embodiments of the present disclosure. The data acquisition module 113 may include detection components 210-1, 210-2, . . . , 210-$k$, . . . , 210-$(n-1)$, 210-$n$ (each of k and n is an integer greater than 1), and a data control panel 220.

At least some of the detection components 210-1, 210-2, . . . , 210-$k$, . . . , 210-$(n-1)$, 210-$n$ may acquire data and send the data to the data control panel 220. The data may include data generated by the radiation module 111, information stored in other storage modules or units of the imaging system 100, etc. As shown in FIG. 2, the detection components 210-1, 210-2, . . . , 210-$k$, . . . , 210-$(n-1)$ may be connected to the data control panel 220 through one or more types of connections, and form one or more channels with the data control panel. The channel may indicate an information transfer mode between a detection component and the data control panel 220. In one channel, a detection component may be directly connected to the data control panel 220. In some embodiments, some of the detection components 210-1, 210-2, . . . , 210-k, . . . , 210-(n−1), 210-n may be connected to the data control panel in parallel (e.g., the detection components 210-1 and 210-2 may be directly connected to the data control panel 220, respectively). In some embodiments, some of the detection components 210-1, 210-2, . . . , 210-k, . . . , 210-(n−1), 210-n may be connected to the data control panel 220 in series (e.g., the detection component 210-3 may be directly connected to the data control panel 220, the detection components 210-4 and 210-3 may be connected in series, and the detection component 210-4 may be connected to the data control panel 220 through the detection component 210-3). In some embodiments, some of the detection components 210-1, 210-2, . . . , 210-k, . . . , 210-(n−1), 210-n may be connected to the data control panel 220 in a combination of series connections and parallel connections (e.g., the detection component 210-1 may be directly connected to the data control panel 220, the detection components 210-2 and 210-3 may be directly connected to the detection component 210-1, respectively, and connected to the data control panel 220 through the detection component 210-1).

The data control panel 220 may send instruction data to the detection components 210-1, 210-2, . . . , 210-k, . . . , 210-(n−1), 210-n and obtain information acquired by the detection components 210-1, 210-2, . . . , 210-k, . . . , 210-(n−1), 210-n. The instruction data may include a configuration command, a clock signal, a sampling triggering command, a feedback command, or the like, or any combination thereof. The detection component 210 may receive the instruction data and perform one or more operations. The operation may include providing location information, performing clock synchronization, acquiring data, transmitting data, providing error information to the data control panel 220, etc.

In some embodiments, the data control panel 220 may further monitor an operation status of the detection components 210-1, 210-2, . . . , 210-k, . . . , 210-(n−1), 210-n and send the operation status to an upper layer software (e.g., a computer program) or generate a document. In some embodiments, if one or more of the detection components 210-1, 210-2, . . . , 210-k, . . . , 210-(n−1), 210-n did not receive instruction data from the data control panel 220, the one or more detection components may return error information to the data control panel 220. The data control panel 220 may record the error count and send the error count to the upper layer software when the error count exceeds a threshold (e.g., a value set by the imaging system 100).

In some embodiments, a channel may include a plurality of detection components connected to the data control panel 220 in series, in parallel, or in a combination thereof, and at least one of the detection components is directly connected to the data control panel 220. The one or more detection components and the data control panel 220 may exchange information (e.g., error information, feedback information, sampling results) through a detection component that is directly connected to the data control panel 220.

For persons having ordinary skills in the art, after understanding the principle of the system, may make variations and modifications on the forms and/or details of the data acquisition module 113 without departing from the principle. However, those variations and modifications are still within the scope of the present disclosure describe above. For example, in some embodiments, the detection components 210-1, 210-2, . . . , 210-k, . . . , 210-(n−1), 210-n may be connected to the data control panel 220 in one or more other variant types of connections based on a parallel connection, a series connection, or a combination thereof.

Figure 3:
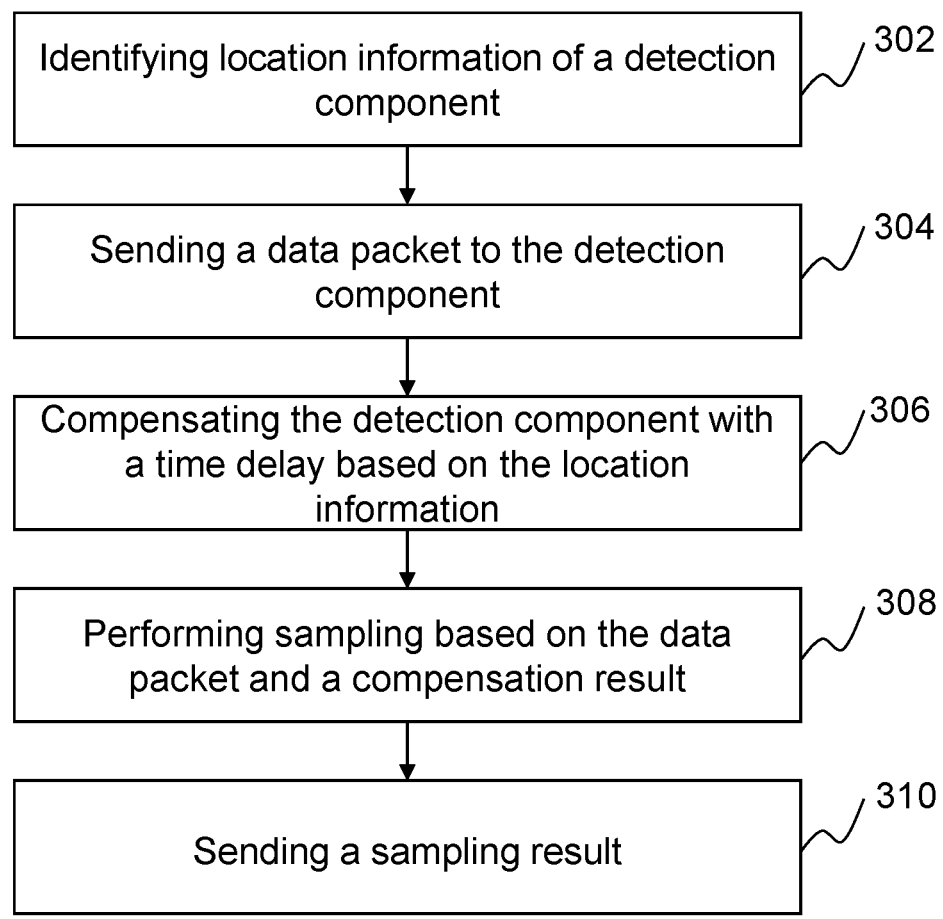
FIG. 3 is a flowchart of an exemplary process for data acquisition according to some embodiments of the present disclosure.

FIG. 3 is a flowchart of an exemplary process for data acquisition according to some embodiments of the present disclosure. In some embodiments, the process for data acquisition may be implemented by the data acquisition module 113. In 302, location information of a detection component may be identified. In some embodiments, 302 may be implemented by the data control panel 220. The location information may include the type of a connection (e.g., in parallel, in series, or in a combination thereof) between the data control panel 220 and the detection component (e.g., one of the 210-1, 210-2, . . . , 210-k, . . . , 210-(n−1), 210-n) and other one or more detection components, an identification number of the detection component (e.g., the data control panel 220 may assign different identification numbers for different detection components, or the manufacturer may set different identification numbers for different detection components), a channel in which the detection component is located, a channel location number of the detection component, or the like, or any combination thereof. The channel may be identified based on a pin of a detection component that is directly connected to the data control panel 220. In some embodiments, the identification of the location information may include identifying a channel, sending a configuration command (e.g., a command of configuration identification number), sending a channel location number, configuring an identification number, etc. (details may be found in the description of FIG. 4).

In 304, a data packet may be sent to the detection component. In some embodiments, 304 may be implemented by the data control panel 220. The data packet may include a clock signal, a sampling triggering command, a command for stopping sampling, or the like, or any combination thereof. The function of the clock signal in the data acquisition module 113 may include synchronization and clock counting. For example, the clock signal may be designated as a reference signal for a sampling start time, a sampling duration, or a time delay compensation. In some embodiments, the frequency of the clock signal may be an integer multiple of a frequency that is used by the one or more detection components for performing simulation integration. The magnitude of the integer multiple may be determined based on a maximum deviation of the integration time that the imaging system 100 can tolerate. In some embodiments, the frequency of the clock signal may be a non-integer multiple of the frequency that is used by the one or more detection components for performing simulation integration, and the frequency of the clock signal may satisfy an index range designed by the imaging system 100. Merely by way of example, the frequency used for simulation integration may be 2.25 MHz. The sampling triggering command may include a sampling duration, etc.

Figure 5:
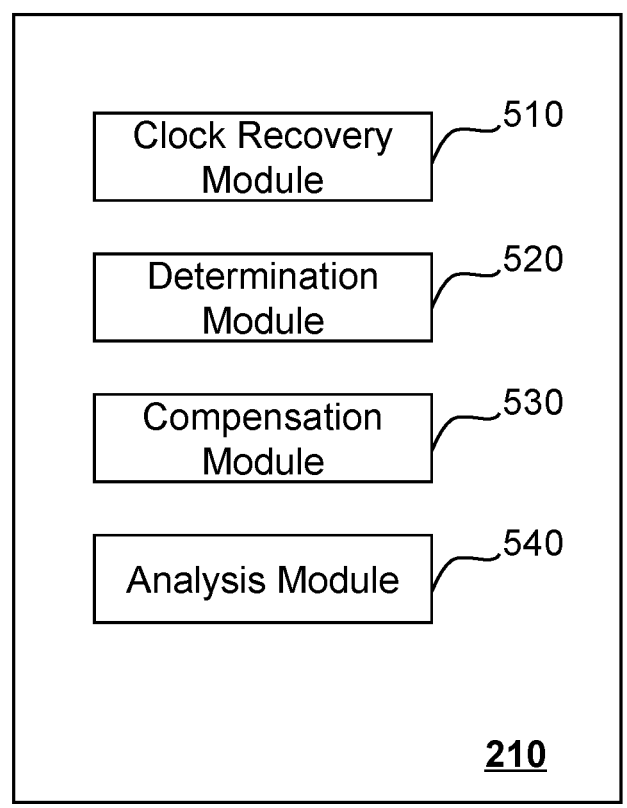
FIG. 5 is a schematic diagram of an exemplary detection component according to some embodiments of the present disclosure.

In 306, the detection component may be compensated with a time delay based on its location information. In some embodiments, 306 may be implemented by a determination module (e.g., a determination module 520 as shown in FIG. 5) and a compensation module (e.g., a compensation module 530 as shown in FIG. 5) of the detection component (e.g., 210-1, 210-2, . . . , 210-k, . . . , 210-(n−1), 210-n). The determination module may identify the type of a connection between the data control panel 220 and the detection component, and return the type of the connection to the compensation module. The compensation module may compensate the detection component with a time delay based on feedback information returned by the determination module.

The time delay may relate to a flight time of a signal to travel on a circuit board and a wire of the system and/or a processing time needed for a function module (e.g., the determination module, the compensation module) of the detection component. In some embodiments, the detection components (e.g., 210-1, 210-2, . . . , 210-$k$, . . . , 210-($n$−1), 210-$n$) may use a same wiring design, and the flight times are the same. The detection components may use the same firmware to ensure that the processing times are the same. In some embodiments, an absolute value of the flight time is small and may be neglected in the time delay compensation. In some embodiments, when two detection components are connected to the data control panel 220 in parallel, the numbers of detection components that the data packet passes through to reach the respective detection components are the same and then the detection components may be compensated with a same time delay. In some embodiments, when two detection components are connected to the data control panel 220 in series, the numbers of detection components that the data packet passes through to reach the respective detection components are different and then the two detection components may be compensated with different time delays. The time delay may be determined based on a fixed value set by the imaging system 100 or by performing a delay measurement instruction.

In some embodiments, the compensation of the detection component with the time delay may include determining a time compensation signal for the detection component, compensating the detection component with the time delay based on the time compensation signal and the clock signal, etc. (details may be found in the description of FIG. 6).

In 308, a sampling may be performed based on the data packet and a compensation result. In some embodiments, the sampling operation may be implemented by the detection component 210. After the detection component is compensated with the time delay, the detection component may trigger a sampling based on a sampling triggering command of the data packet. In some embodiments, the sampling triggering command may include a sampling duration, and the detection component may perform counting based on the clock signal of the data packet. When the counting reaches the sampling duration, the sampling is stopped automatically. In some embodiments, after the detection component triggers the sampling, the detection component may stop sampling based on an instruction for stopping sampling. The instruction for stopping sampling may be sent by the data control panel 220. In some embodiments, as similar to the description of 306, a compensation module (e.g., the compensation module 530 shown in FIG. 5) of the detection component (e.g., 210-1, 210-2, . . . , 210-$k$, . . . , 210-($n$−1), 210-$n$) may compensate the instruction for stopping sampling with a time delay based on the type of the connection between the data control panel 220 and the detection component.

In 310, a sampling result obtained in 308 may be sent to the data control panel 220. In some embodiments, the sampling result may be sent to the data control panel 220 by the detection component. The sampling result may include scanning data of the scanned object, etc.

For persons having ordinary skills in the art, after understanding the principle of data acquisition, may make variations and modifications on the forms and details of the ways and operations of data acquisition without departing from the principle. However, those variations and modifications are still within the scope of the claims of the present disclosure. In some embodiments, the process described above may include other operations, for example, intermediate processing results and/or final processing results of the above process may be stored, and storage locations may be modules or units having a storage function in the imaging system 100. In some embodiments, the data control panel 220 may send the sampling result in 310 to an upper layer software (e.g., a computer program) or generate a document.

Figure 4:
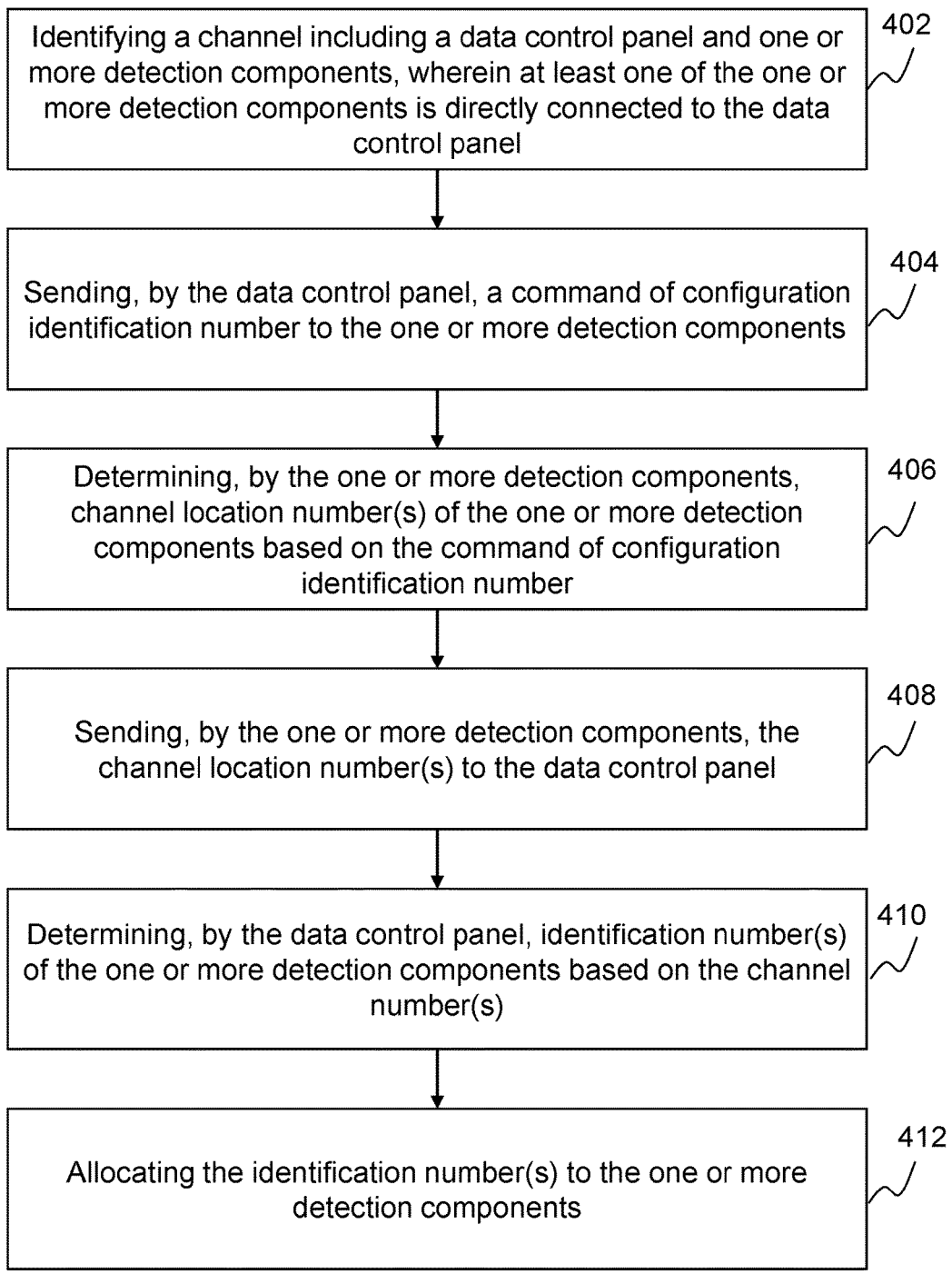
FIG. 4 is a flowchart of an exemplary configuration method according to some embodiments of the present disclosure.

FIG. 4 is a flowchart of an exemplary configuration method according to some embodiments of the present disclosure. In some embodiments, the configuration method 400 may be implemented by the data acquisition module 113. In 402, a channel may be identified. The channel may include a data control panel and one or more detection components. In some embodiments, the channel may include a plurality of detection components, at least one detection component may be directly connected to data control panel, and the plurality of detection components may be connected to the data control panel 220 in series, in parallel, or in a combination thereof. In some embodiments, the channel may be identified by the data control panel 220. The data control panel 220 may further send data or instructions to the detection components based on channel information. In some embodiments, the channel may be identified based on a pin of a detection component that is directly connected to the data control panel.

In 404, the data control panel may send a command of configuration identification number to the one or more detection components. In some embodiments, the data control panel may send the command of configuration identification number to the one or more detection components by broadcast.

In 406, the one or more detection components may determine channel location number(s) of the one or more detection components based on the command of configuration identification number. In some embodiments, the channel location number(s) of the one or more detection components (e.g., some of 210-1, 210-2, . . . , 210-$k$, . . . , 210-($n$−1), 210-$n$) in the channel may be different. In some embodiments, different channel location numbers indicate different locations of the detection components in the channel. For example, in a channel, the detection component 210-4 and the detection component 210-3 are connected in series, the detection component 210-3 is directly connected to the data control panel 220, and the detection component 210-4 is connected to the data control panel 220 through the detection component 210-3 so that different channel location numbers of the detection components 210-3 and the detection component 210-4 may indicate locations of the detection component 210-3 and the detection component 210-4 in the channel and a location relationship with the data control panel 220. Further, in some embodiments, the channel location numbers may be continuous numbers, and the continuous numbers may be numerals, letters, underscores, or the like, or a combination thereof.

In 408, the one or more detection components may send the channel location number(s) to the data control panel. In 410, the data control panel may determine identification number(s) of the one or more detection components based on the channel location number(s). In some embodiments, the identification numbers may be used as a basis for determining the type of the connection (e.g., in parallel, in series, or in a combination thereof) between the data control panel and the plurality of detection components. The identification number(s) of the one or more detection components may be calculated based on the channel location number(s) determined in 408, or selected from an identification number set based on the channel location number(s).

In 412, the identification number(s) may be allocated to the one or more detection components. In some embodiments, the data control panel 220 may allocate the identification number(s) to the one or more detection components. The identification number(s) and information corresponding to the detection component(s) may be recorded in a specific storage element, and may be accessed by the data control panel 220, the one or more detection components, or other components of the imaging system 100.

For persons having ordinary skills in the art, after understanding the principle of the configuration method, may make variations and modifications on the forms and details of the ways and operations of the configuration without departing from the principle. However, those variations and modifications are still within the scope of the claims of the present disclosure. In some embodiments, some operations of the process described above may be combined into one operation, for example, 406 and 408, the determination of the channel location number(s) and the sending of the channel location number(s) may be implemented in one operation. In some embodiments, the process may also include other operations, for example, after 404, when some of the one or more detection components did not receive the command of configuration identification number, the some of the one or more detection components may send error information to the data control panel 220. The data control panel 220 may record the error count and send the error count to an upper layer software (e.g., a computer program) or generate a document when the error count exceeds a threshold (e.g., a value set by the imaging system 100). Further, after 412, the data control panel may send the identification number(s) to the upper layer software.

FIG. 5 is a schematic diagram of an exemplary detection component according to some embodiments of the present disclosure. The detection component 210 may include a clock recovery module 510, a determination module 520, a compensation module 530, and an analysis module 540. The clock recovery module 510 may identify a clock signal. In some embodiments, the clock recovery module 510 may identify the clock signal based on the Clock and Data Recovery (CDR) technology. The function of the clock signal in the data acquisition module 113 may include synchronization and clock counting. For example, the clock signal may be designated as a reference signal for a sampling start time, a sampling duration, or a time delay compensation. In some embodiments, the frequency of the clock signal may be an integer multiple of a frequency that is used by the one or more detection components for performing simulation integration. The magnitude of the integer multiple may be determined based on a maximum deviation of the integration time that the imaging system 100 can tolerate. In some embodiments, the frequency of the clock signal may be a non-integer multiple of the frequency that is used by the one or more detection components for performing simulation integration, and the frequency of the clock signal may satisfy an index range designed by the imaging system 100. Merely by way of example, the frequency for simulation integration may be 2.25 MHz.

The determination module 520 may determine the type of a connection between the data control panel 220 and the detection component (e.g., one or more of the detection components 210-1, 210-2, . . . , 210-$k$, . . . , 210-($n$–1), 210-$n$) and send the type of the connection to the compensation module 530. As shown in FIG. 2, some of the detection components 210-1, 210-2, . . . , 210-$k$, . . . , 210-($n$–1), 210-$n$ may be connected to the data control panel 220 in parallel, in series, or in a combination thereof.

The compensation module 530 may compensate the detection component with a time delay based on the type of the connection between the data control panel 220 and the detection component(s) (e.g., 210-1, 210-2, . . . , 210-$k$, . . . , 210-($n$–1), 210-$n$). The time delay may relate to a flight time of a signal to travel on a circuit board and a wire of the system and/or a processing time needed for the clock recovery module 510, the determination module 520, the compensation module 530, and the analysis module 540 of the detection component. In some embodiments, the detection components (e.g., 210-1, 210-2, . . . , 210-$k$, . . . , 210-($n$–1), 210-$n$) may use a same wiring design, and the flight times are same. The detection components may use the same firmware to ensure the processing times are the same. In some embodiments, when two detection components are connected to the data control panel 220 in parallel, the numbers of detection components that the data packet passes through to reach the respective detection components may be the same and then the detection components may be compensated with a same time delay. In some embodiments, when two detection components are connected to the data control panel 220 in series, the numbers of the detection components that the data packet passes through to reach the respective detection components may be different and then the detection components may be compensated with different time delays. The time delay may be determined based on a fixed value set by the imaging system 100 or by performing a delay measurement instruction. In some embodiments, the compensation module 530 may compensate the detection component with the time delay based on the time compensation signal and the clock signal.

The analysis module 540 may identify a sampling triggering command. In some embodiments, the sampling triggering command may include a sampling start time and/or a sampling duration, etc.

For persons having ordinary skills in the art, after understanding the principle of the detection component, may make variations and modifications on the forms and details of the detection component 210 without departing from the principle. However, those variations and modifications are still within the scope of the present disclosure. For example, in some embodiments, the determination module 520 and compensation module 530 may be combined into one module. In some embodiments, the detection component 210 may include one or more storage modules.

Figure 6:
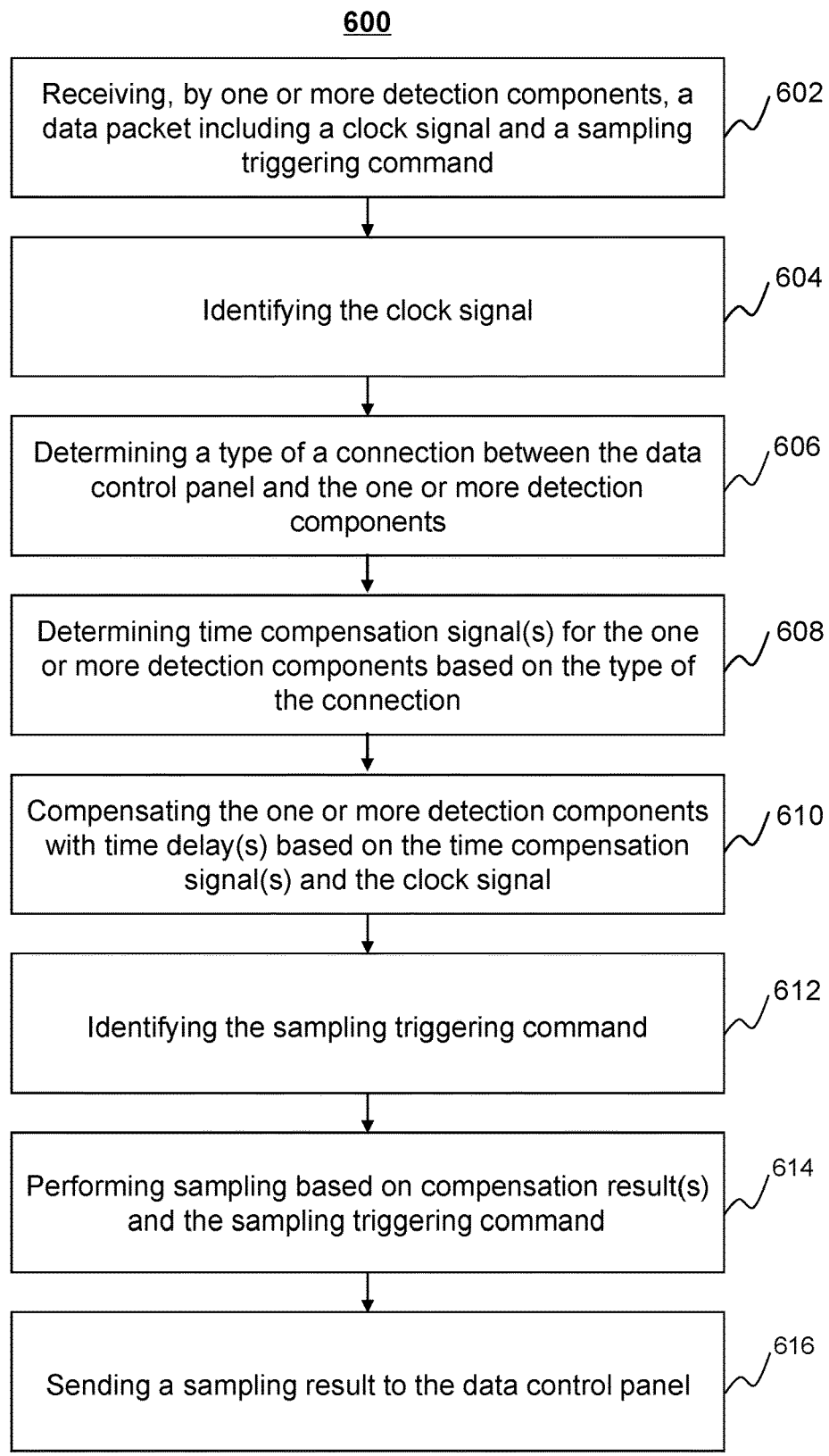
FIG. 6 is a flowchart of an exemplary process for data acquisition according to some embodiments of the present disclosure.

FIG. 6 is a flowchart of an exemplary process for data acquisition according to some embodiments of the present disclosure. In some embodiments, the process 600 for data acquisition may be implemented by the data acquisition module 113. In some embodiments, 304-310 in FIG. 3 may be performed according to process 600.

In 602, one or more detection components may receive a data packet including a clock signal and a sampling triggering command. As described above, the function of the clock signal may be synchronization and clock counting in the data acquisition module 113. In some embodiments, the clock signal may be designated as a reference signal for a sampling start time, a sampling duration, and/or a time delay compensation. In some embodiments, the sampling triggering command may include a sampling start time and/or a sampling duration.

In 604, the clock signal may be identified. In some embodiments, 604 may be implemented by the clock recovery module 510. The identification of the clock signal may include extracting the clock signal from the data packet, converting the clock signal into a format that the detection component can recognize, etc. In some embodiments, the identification of the clock signal may be implemented based on the Clock and Data Recovery (CDR) technology.

In 606, the type of a connection between the data control panel 220 and the one or more detection components may be determined. In some embodiments, the plurality of detection components may be connected to the data control panel 220 in parallel, in series, or in a combination thereof. In some embodiments, the type of the connection between the data control panel 220 and the one or more detection components may be determined based on the identification number(s) of the one or more detection components (details may be found in the description of FIG. 7). In some embodiments, the type of the connection between the data control panel 220 and the one or more detection components may be determined based on a relative location of the one or more detection components with respect to a characteristic detection component (details may be found in the description of FIG. 8).

In 608, time compensation signal(s) may be determined for the one or more detection components based on the type of the connection between the data control panel 220 and the one or more detection components. In some embodiments, 608 may be implemented by the compensation module 530. The compensation signal(s) may relate to the type of the connection between the data control panel 220 and the one or more detection components. In some embodiments, when the plurality of detection components are connected to the data control panel 220 in parallel, the plurality of detection components may be compensated with a same time delay. In some embodiments, when the plurality of detection components are connected to the data control panel 220 in series, the plurality of detection components may be compensated with different time delays. The compensation signal may be determined based on a flight time of a signal to travel on a circuit board and a wire of the system, a processing time needed for the clock recovery module 510, the determination module 520, the compensation module 530, and the analysis module 540 of the detection component, etc.

In 610, the one or more detection components may be compensated with time delay(s) based on the time compensation signal(s) and the clock signal. In some embodiments, 610 may be implemented by the compensation module 530. In some embodiments, the time compensation signal(s) and the clock signal may form new time control signal(s), and the one or more detection components may perform subsequent operations based on the new time control signal(s).

In 612, the sampling triggering command may be identified. In some embodiments, 612 may be implemented by the analysis module 540. The identification of the sampling triggering command may include extracting the sampling triggering command from the data packet, converting the sampling triggering command into a format that the detection component can recognize, etc.

In 614, the one or more detection components may perform sampling based on a compensation result generated in 610 and the sampling triggering command. After the time delay compensation for the one or more detection components is completed, the one or more detection components may trigger sampling based on the sampling triggering command. In some embodiments, the sampling triggering command may include a sampling duration, and the one or more detection components may perform time counting based on the clock signal. When the time counting reaches the sampling duration, the sampling may be stopped automatically. In some embodiments, after the one or more detection components trigger sampling, the one or more detection components may stop sampling based on an instruction for stopping sampling. The instruction for stopping sampling may be sent by the data control panel 220. In some embodiments, as similar to the description of 608 and 610, the compensation module 530 of the detection component (e.g., 210-1, 210-2, . . . , 210-$k$, . . . , 210-($n$−1), 210-$n$) may compensate the instruction for stopping sampling with a time delay based on the type of the connection between the data control panel 220 and the one or more detection components.

In 616, a sampling result obtained in 614 may be sent to the data control panel 220. In some embodiments, 616 may be implemented by the detection component 210. The sampling result may include scanning data of the scanned object, etc.

For persons having ordinary skills in the art, after understanding the principle of data acquisition, may make variations and modifications on the forms and details of the ways and operations of data acquisition without departing from the principle. However, those variations and modifications are still within the scope of the claims of the present disclosure. In some embodiments, some operations of the process described above may be combined into one operation, for example, 608 and 610 (determining the compensation signal and compensating with the time delay) may be implemented in one operation. In some embodiments, the process may also include other operations, for example, intermediate processing results and/or final processing results generated in the operations may be stored, and storage locations may be modules or units having a storage function in the imaging system 100. In some embodiments, after 616, the data control panel 220 may send the sampling result to an upper layer software (e.g., a computer program) or generate a document.

Figure 7:
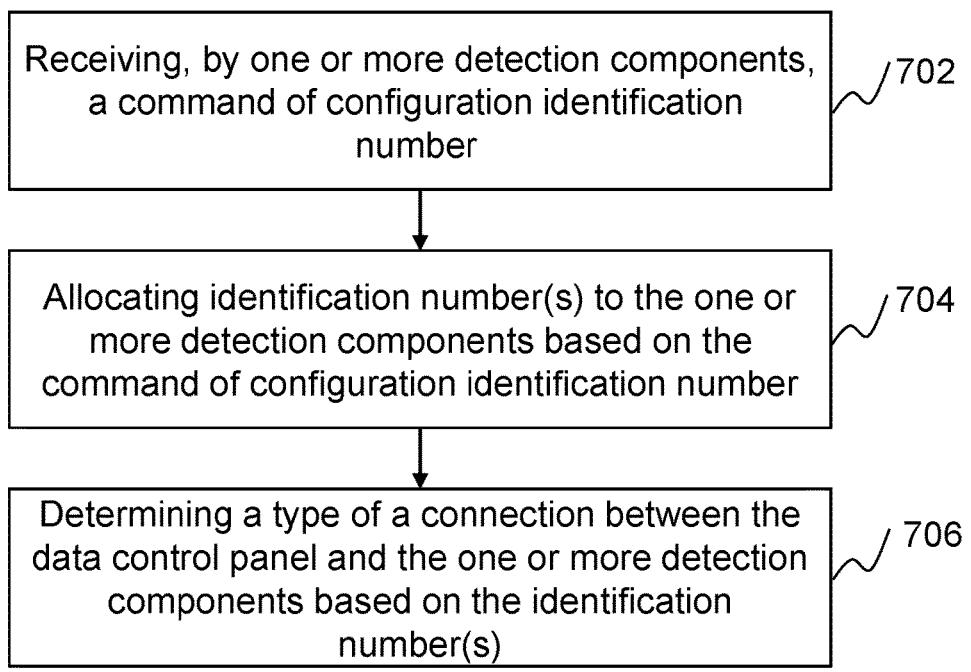
FIG. 7 is a flowchart of an exemplary process for determining the type of a connection between a data control panel and a detection component according to some embodiments of the present disclosure.

FIG. 7 is a flowchart of an exemplary process for determining the type of a connection between the data control panel and the detection component. In some embodiments, the process 700 for determining the type of the connection between the data control panel and the detection component may be implemented by the data acquisition module 113. In 702, one or more detection components may receive a command of configuration identification number. In some embodiments, the command of configuration identification number may be sent by the data control panel 220. For example, the data control panel 220 may send the command of configuration identification number to the one or more detection components (e.g., 210-1, 210-2, . . . , 210-$k$, . . . , 210-($n$−1), 210-$n$) by broadcast.

In 704, the data control panel 220 may allocate identification number(s) to the one or more detection components based on the command of configuration identification number. In some embodiments, as similar to the description of FIG. 4, the allocation of the identification number(s) may include determining channel location number(s) of the one or more detection components, determining identification number(s) of the one or more detection components based on the channel location number(s), allocating the identification number(s) to the one or more detection components, etc.

In 706, the type of a connection between the data control panel 220 and the one or more detection components may be determined based on the identification number(s). In some embodiments, 706 may be implemented by the determination module 520. In some embodiments, the type of the connection between the data control panel 220 and the one or more detection components may be determined based on the identification number(s). For example, the identification number(s) may include location information of the one or more detection components and the type of the connection between the data control panel 220 and the one or more detection components (e.g., in parallel, in series, in combination thereof). In some embodiments, the type of the connection between the data control panel 220 and the one or more detection components may be determined based on the relationship among the identification number(s) of the one or more detection components.

Figure 8:
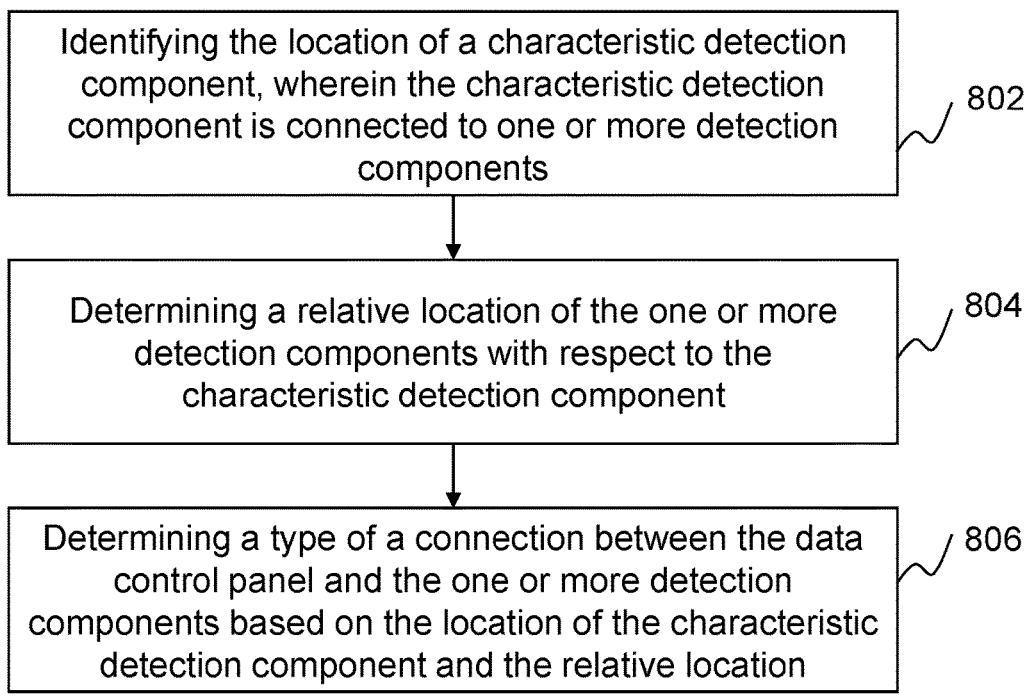
FIG. 8 is a flowchart of an exemplary process for determining the type of a connection between a data control panel and a detection component according to some embodiments of the present disclosure.

FIG. 8 is a flowchart of an exemplary process for determining the type of a connection between the data control panel and the detection component. In some embodiments, process 800 for determining the type of the connection between the data control panel and the detection component may be implemented by the data acquisition module 113. In 802, the location of a characteristic detection component may be identified, wherein the characteristic detection component is connected to one or more detection components. In some embodiments, 802 may be implemented by the data control panel 220. The characteristic detection component may be a detection component that is directly connected to the data control panel 220, or a detection component that is connected to other detection components in series and then connected to the data control panel 220. In some embodiments, the characteristic detection component may be one or more of the detection components 210-1, 210-2, . . . , 210-$k$, . . . , 210-($n$−1), 210-$n$ with known location information. The location information may include an identification number (e.g., an identification number of the characteristic detection component allocated by the data control panel 220, an identification number set by the manufacturer) of the characteristic detection component, a channel in which the characteristic detection component is located, a channel location number of the characteristic detection component in the channel, or the like, or any combination thereof.

In 804, a relative location of the one or more detection components with respect to the characteristic detection component may be determined based on the characteristic detection component. In some embodiments, 804 may be implemented by the characteristic detection component. In some embodiments, the relative location may include a topological relationship (e.g., a bus topology, a tree topology, a ring topology, a mesh topology, a star topology, etc.) between the characteristic detection component and the one or more detection components in the imaging system 100, the type of a connection (e.g., in parallel, in series, or in a combination thereof) between the data control panel 220 and the one or more detection components and the characteristic detection component.

In 806, the type of the connection between the data control panel 220 and the one or more detection components may be determined based on the location of the characteristic detection component and the relative location. In some embodiments, 806 may be implemented by the determination module 520. In some embodiments, the type of the connection between the data control panel 220 and the one or more detection components may be determined based on the identification number of the characteristic detection component and the relative location of the one or more detection components with respect to the characteristic detection component.

In some embodiments, in 806, time compensation signal(s) of the one or more detection components may be determined based on the relative location and a time compensation signal of the characteristic detection component. For example, a detection component and the characteristic detection component are connected to the data control panel 220 in series and a time compensation signal of the detection component may be determined based on the time compensation signal of the characteristic detection component.

Figure 9:
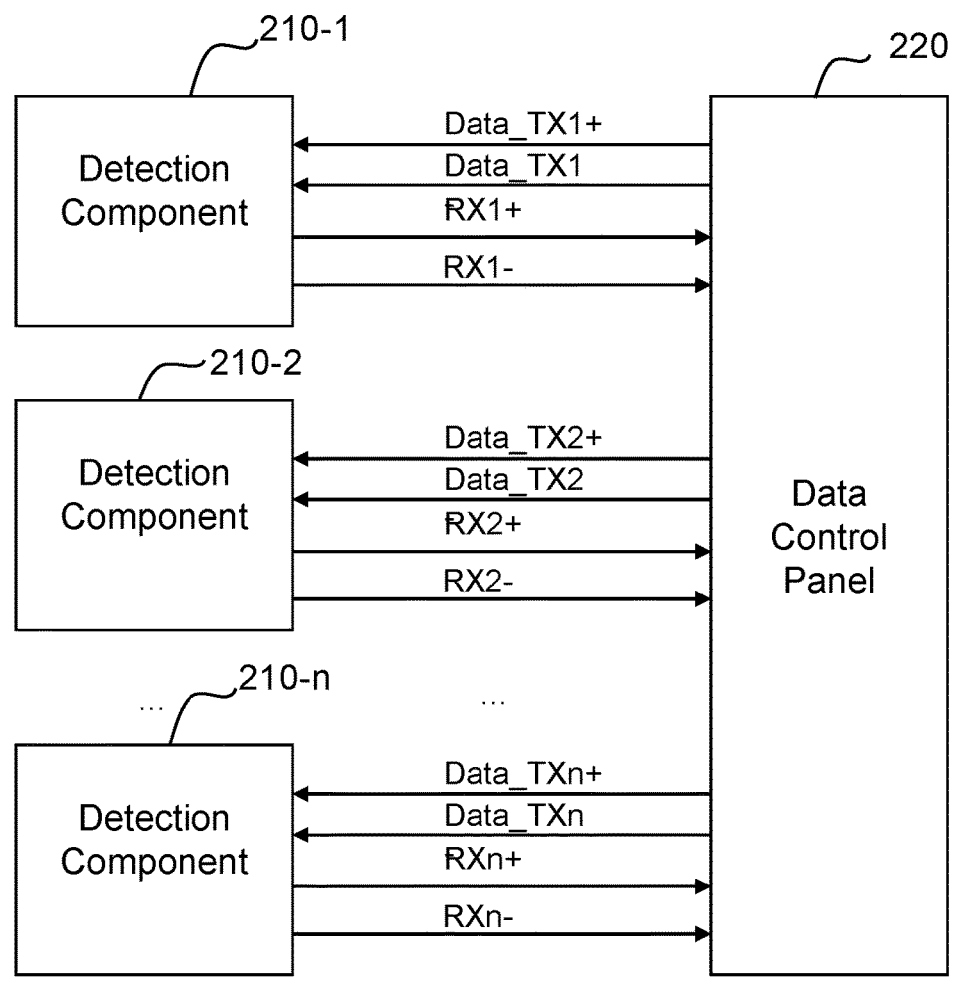
FIG. 9 is a schematic diagram of an exemplary data acquisition module when a plurality of detection components are connected to a data control panel in parallel according to some embodiments of the present disclosure.

FIG. 9 is a schematic diagram of an exemplary data acquisition module when the plurality of detection components are connected to the data control panel in parallel according to some embodiments of the present disclosure. As shown in FIG. 9, detection components 210-1, 210-2, . . . , 210-$n$ ($n$ may represent an integer greater than 1) are connected to the data control panel 220 in parallel, and the detection components 210-1, 210-2, . . . , 210-$n$ are directly connected to the data control panel 220, respectively. The data control panel 220 may send command data packets Data_TX1+, Data_TX2+, . . . , Data_TXn+, Data_TX1−, Data_TX2−, . . . , Data_Txn− ($n$ may represent an integer greater than 1) to the detection components. The command data packet may include a clock signal, a sampling triggering command, a command of configuration identification number, an instruction for stopping sampling, or the like, or any combination thereof. The detection components 210-1, 210-2, . . . , 210-$n$ may send feedback data packets RX1+, RX2+, . . . , RXn+, RX1−, RX2−, . . . , RXn− ($n$ may represent an integer greater than 1) to the data control panel 220. The feedback data packets RX1+, RX2+, . . . , RXn+, RX1−, RX2−, . . . , RXn− may include location information (e.g., a channel in which the detection component is located), a sampling result (e.g., scanning data), error information, or the like, or any combination thereof. Further, the data control panel 220 may send the feedback data packets to an upper layer software (e.g., a computer program) or generate a document.

In some embodiments, the command data packets Data_TX1+, Data_TX2+, . . . , Data_TXn+, Data_TX1−, Data_TX2−, . . . , Data_Txn− sent by the data control panel 220 may include a clock signal and a sampling triggering command. The clock signal is related to controlling a time point when the detection component acquires a signal. In some embodiments, the clock signals sent by the data control panel 220 to different detection components may be the same or different. Further, the clock signals of different detection components may depend on locations and the type of the connection of the detection components. The detection components 210-1, 210-2, 210-$n$ may identify the clock signals and the sampling triggering commands, compensate the detection components with time delays, and perform sampling based on compensation results and the sampling triggering commands, and send the sampling results RX1+, RX2+, . . . , RXn+, RX1−, RX2−, . . . , RXn− to the data control panel 220. In some embodiments, the wiring designs, types, and firmware of the detection components 210-1, 210-2, . . . , 210-$n$ that are connected to the data control panel 220 in parallel may be all the same, the flight times of a signal to travel on the circuit boards and wires of the systems and the processing times of the detection components may be all the same, then the detection components may be compensated with a same time delay. In some embodiments, if the wiring designs of two detection components (e.g., detection component 210-1 and detection component 210-2) are the same, the flight times of a signal to travel on the circuit boards and wires of the systems may be the same, whereas the types and firmware of the two detection components may be different, and processing times of the two detection components may be different, then the two detection components may be compensated with different time delays. In some embodiments, the absolute value of the flight time is small and may be neglected in the time delay compensation.

Figure 10:
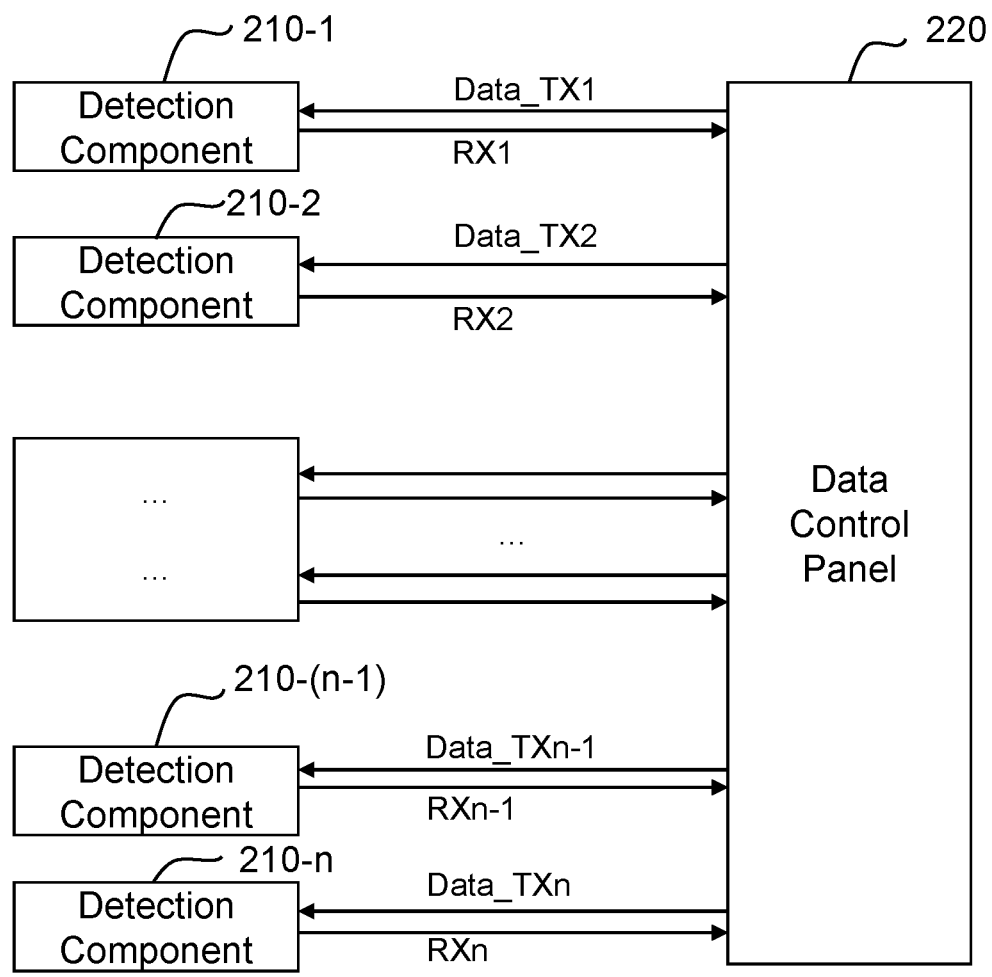
FIG. 10 is a schematic diagram of an exemplary data acquisition module when a plurality of detection components are connected to a data control panel in parallel according to some embodiments of the present disclosure.

FIG. 10 a schematic diagram of an exemplary data acquisition module when the plurality of detection components are connected to the data control panel in parallel according to some embodiments of the present disclosure. As shown in FIG. 10, detection components 210-1, 210-2, . . . , 210-n (n may represent an integer greater than 1) are connected to the data control panel 220 in parallel, and the detection components 210-1, 210-2, . . . , 210-n are directly connected to the data control panel 220 respectively. The data control panel 220 may send command data packets Data_TX1+, Data_TX2+, . . . , Data_TXn+, Data_TX1−, Data_TX2−, . . . , Data_Txn− (n may represent an integer greater than 1) to the detection components. Merely by way of example, the data packet Data_TX1 may include data sent by Data_TX1+ and Data_TX1− illustrated in FIG. 9, or data sent by the data control panel to the detection component as described elsewhere in the present disclosure. Further, the detection components may send feedback data packets RX1, RX2, . . . , RXn−1, RXn (n represent an integer greater than 1) to the data control panel 220. Merely by way of example, the feedback data packet RX1 may include data sent by RX1+ and RX1− illustrated in FIG. 9, or data sent by the detection components to the data control panel as described elsewhere in the present disclosure.

Figure 11:
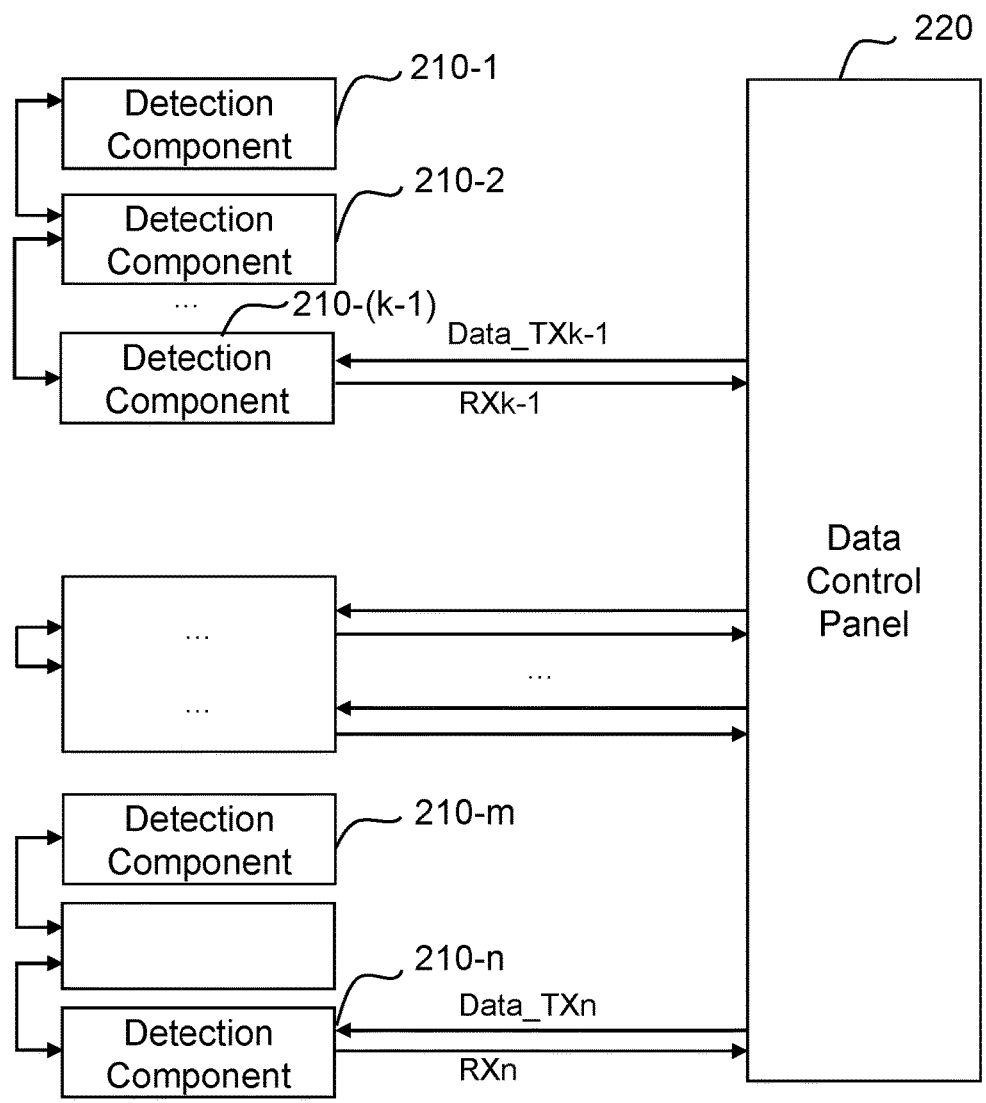
FIG. 11 is a schematic diagram of an exemplary data acquisition module when a plurality of detection components are connected to a data control panel in a combination of series connections and parallel connections according to some embodiments of the present disclosure.

FIG. 11 is a schematic diagram of an exemplary data acquisition module when the plurality of detection components are connected to the data control panel in a combination of series connections and parallel connections according to some embodiments of the present disclosure. As shown in FIG. 11, detection components 210-1, 210-2, . . . , 210-(k−1) (k may represent an integer greater than 1) are connected to the data control panel 220 in series, the detection component 210-(k−1) is directly connected to the data control panel 220, and the detection components 210-1, 210-2, . . . , are connected to the data control panel 220 through the detection component 210-(k−1). The detection components 210-m, . . . , 210-n (each of m and n may represent an integer greater than 1) are connected to the data control panel 220 in series, the detection component 210-n is directly connected to the data control panel, and the detection components 210-m, . . . , are connected to the data control panel 220 through the detection component 210n. Similarly, other detection components may be connected to the data control panel 220 in parallel (e.g., detection components 210-5 and 210-6 are directly connected to the data control panel 220) or in series. The working process between the detection components 210-1, 210-2, . . . , 210-(k−1), . . . , 210-m, . . . , 210-n and the data control panel 220 is the similar to that described in FIG. 9. In some embodiments, the detection components 210-1, 210-2, . . . , 210-(k−1), . . . , 210-m, . . . , 210-n may use the same wiring design and the flight times of a signal to travel on the circuit boards and wires of the systems may be the same. The types and firmware of the detection components are the same so that the processing times of the detection components may be the same. In some embodiments, two detection components may be compensated with a same time delay when the two detection components are connected to the data control panel 220 in parallel. In some embodiments, two detection components may be compensated with different time delays when the two detection components are connected to the data control panel 220 in series. For example, detection component 210-3 is directly connected to the data control panel 220, detection components 210-4 and 210-5 are directly connected to the detection component 210-3, respectively, and are connected to the data control panel 220 through the detection component 210-3. The time delay with which the detection component 210-3 is compensated may be T3, and the time delay with which the detection components 210-4 and 210-5 are compensated may be T3-C1. Similar to T1 and C, T3 and C1 represent time values.

Figure 12:
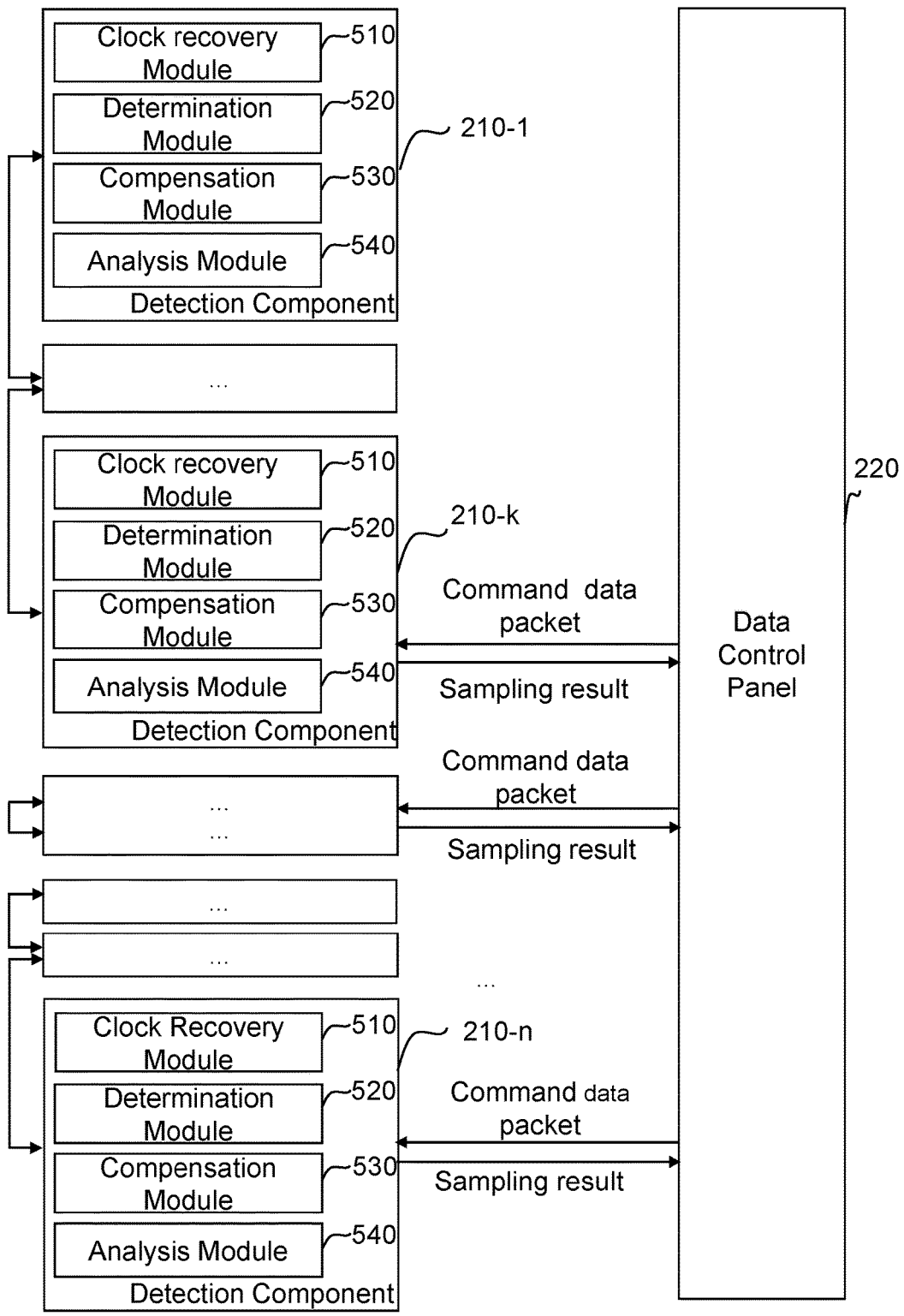
FIG. 12 is a schematic diagram of an exemplary data acquisition module when a plurality of detection components are connected to a data control panel in a combination of series connections and parallel connections according to some embodiments of the present disclosure.

FIG. 12 is a schematic diagram of an exemplary data acquisition module when the plurality of detection components are connected to the data control panel in a combination of series connections and parallel connections according to some embodiments of the present disclosure. The data acquisition module may include detection components 210-1, . . . , 210-k, . . . , 210-n (each of k and n may represent an integer greater than 1) and a data control panel 220. The detection component 210 may include a clock recovery module 510, a determination module 520, a compensation module 530, and an analysis module 540.

As shown in FIG. 12, the detection components 210-1, . . . , 210-k, . . . , 210-n are connected to the data control panel 220, and form a plurality of channels with the data control panel 220. For example, the detection components 210-1, . . . , 210-k and the data control panel 220 form a first channel. In the first channel, the detection components 210-1, . . . , 210-k are connected in series, and the detection component 210-k is directly connected to the data control panel 220. The data control panel 220 may identify the first channel through a pin of the detection component 210-k. In the first channel, the detection components 210-1, . . . , 210-k may correspond to different channel location numbers, wherein the channel location numbers may be continuous numbers. The continuous numbers may be numerals, letters, underscores, or the like, or a combination thereof. In the first channel, the detection components 210-1, . . . , 210-k and the data control panel 220 may exchange information (e.g., a command data packet) through the detection component 210-k. Similarly, the detection component 210-n and other one or more detection components may be connected to the data control panel 220 in parallel, in series, or in a combination thereof and form an Nth channel (N may represent an integer greater than 1), wherein the detection component 210-n is directly connected to the data control panel 220.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of some patentable classes or context including any new and useful process, machine, manufacture, or composition of matter, or any new and useful improvement thereof. Accordingly, aspects of the present disclosure may be implemented entirely hardware, entirely software (including firmware, resident software, microcode, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters outlined in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values outlined in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:
1. A method comprising:
identifying a channel including a data control panel and one or more detection components, wherein at least one of the one or more detection components is directly connected to the data control panel;
sending, by the data control panel, a configuration command to the one or more detection components;
sending, by the one or more detection components, one or more channel location numbers of the one or more detection components to the data control panel based on the configuration command;
determining, by the data control panel, one or more identification numbers for the one or more detection components based on the one or more channel location numbers;

allocating, by the data control panel, the one or more identification numbers to the one or more detection components;

identifying, by the one or more detection components, a type of a connection between the data control panel and the one or more detection components based on the one or more identification numbers; and determining, by the one or more detection components, one or more time compensation signals for the one or more detection components based on the type of the connection.

2. The method of claim 1, wherein identifying the channel comprises:

identifying the channel based on a pin of a detection component that is directly connected to the data control panel.

3. The method of claim 1, wherein the channel comprises a plurality of detection components, and wherein the plurality of detection components are connected to the data control panel in parallel, in series, or in a combination thereof.

4. The method of claim 1, wherein sending, by the data control panel, the configuration command to the one or more detection components comprises:

sending, by the data control panel, the configuration command by broadcast.

5. The method of claim 1, further comprising:

sending, by the data control panel, the one or more identification numbers to an upper layer software.

6. The method of claim 1, wherein the channel comprises a plurality of detection components, and wherein the channel location numbers of the plurality of detection components are different from each other.

7. The method of claim 1, wherein the channel comprises a plurality of detection components, and wherein the channel location numbers of the plurality of detection components are continuous.

8. The method of claim 1, further comprising:

receiving, by the one or more detection components, a data packet including a clock signal and a sampling triggering command;

performing, by the one or more detection components, sampling based on the one or more time compensation signals, the clock signal, and the sampling triggering command; and sending, by the one or more detection components, a sampling result to the data control panel.

9. The method of claim 8, further comprising:

identifying, by the one or more detection components, the clock signal based on the Clock and Data Recovery (CDR) technology.

10. The method of claim 8, wherein a frequency of the clock signal is an integer multiple of a frequency that is used by the one or more detection components for performing simulation integration.

11. The method of claim 3, where the determining the one or more time compensation signals comprises:

compensating the plurality of detection components with a same time delay when the plurality of detection components are connected to the data control panel in parallel; and compensating the plurality of detection components with different time delays when the plurality of detection components are connected to the data control panel in series.

12. A device comprising:

a channel including a data control panel and one or more detection components, wherein at least one of the one or more detection components is directly connected to the data control panel, wherein, the data control panel is configured to:
identify the channel; and
send a configuration command to the one or more detection components;

the one or more detection components are configured to:
determine one or more channel location numbers of the one or more detection components based on the configuration command, and
send the one or more channel location numbers to the data control panel;

the data control panel is further configured to:
determine one or more identification numbers for the one or more detection components based on the one or more channel location numbers of the one or more detection components; and
allocate the one or more identification numbers to the one or more detection components;

the one or more detection components are further configured to:
identify a type of a connection between the data control panel and the one or more detection components based on the one or more identification numbers; and
determine one or more time compensation signals for the one or more detection components based on the type of the connection.

13. The device of claim 12, wherein the data control panel is further configured to:

identify the channel based on a pin of a detection component that is directly connected to the data control panel.

14. The device of claim 12, wherein the channel comprises a plurality of detection components, wherein the plurality of detection components are connected to the data control panel in parallel, in series, or in a combination thereof.

15. The device of claim 12, wherein to send the configuration command to the one or more detection components, the data control panel is further configured to:

send the configuration command by broadcast.

16. The device of claim 12, wherein the channel comprises a plurality of detection components, and wherein the channel location numbers of the plurality of detection components are different from each other.

17. The device of claim 12, wherein the channel comprises a plurality of detection components, and wherein the channel location numbers of the plurality of detection components are continuous.

18. The device of claim 12, wherein the data control panel is further configured to send the one or more identification numbers to an upper layer software.

19. The device of claim 12, wherein the one or more detection components are further configured to:

receive a data packet from the data control panel, the data packet including a clock signal and a sampling triggering command;

perform sampling based on the one or more compensation signals, the clock signal, and the sampling triggering command; and send a sampling result to the data control panel.

20. The device of claim 19, wherein the one or more detection components are further configured to: identify the clock signal based on the Clock and Data Recovery (CDR) technology.

* * * * *